United States Patent [19]

Bernstein

[11] Patent Number: 4,466,968
[45] Date of Patent: Aug. 21, 1984

[54] METHOD FOR PROPHYLAXIS OR TREATMENT OF EMESIS AND NAUSEA

[75] Inventor: Joel E. Bernstein, Deerfield, Ill.

[73] Assignee: Dermall, Ltd., Northbrook, Ill.

[21] Appl. No.: 310,103

[22] Filed: Oct. 9, 1981

Related U.S. Application Data

[63] Continuation-in-part of Ser. No. 209,398, Nov. 24, 1980, abandoned.

[51] Int. Cl.³ ............................................ A61K 31/485
[52] U.S. Cl. .................................................... 424/260
[58] Field of Search .......................................... 424/260

[56] References Cited

U.S. PATENT DOCUMENTS 3,254,088  5/1966  Lewenstein ..................... 424/260
3,332,950  7/1967  Blumberg ........................ 424/260
4,181,726  1/1980  Bernstein ........................ 424/260

OTHER PUBLICATIONS

Physicians Desk Reference, 33, (1979), p. 867.

*Primary Examiner*—Stanley J. Friedman
*Attorney, Agent, or Firm*—Ronald A. Sandler

[57] ABSTRACT

An improved method of treating nausea and/or emesis or vomiting and the like comprising administering an effective dosage of naloxone or n-methyl cyclopropyl naloxone for their pharmaceutically acceptable salts to a patient suffering from such nausea and/or emesis.

9 Claims, No Drawings

METHOD FOR PROPHYLAXIS OR TREATMENT OF EMESIS AND NAUSEA

RELATED APPLICATIONS

This is a continuation-in-part of my copending application, Ser. No. 209,398 filed Nov. 24, 1980, now abandoned titled METHOD FOR PREVENTING AND/OR TREATING EMESIS AND NAUSEA.

BACKGROUND OF THE INVENTION

Emesis or vomiting is a common symptom of a variety of gastrointestinal or central nervous system disorders. Therapy is generally oriented at removing the offending stimulus or resolving the condition responsible for the vomiting. Emesis is often, but not always, accompanied by nausea, an unpleasant subjective gastrointestinal sensation which provokes the feeling that one has to vomit. Pharmacological or medicinal remedies for nausea and vomiting are few and of limited usefulness, and include the phenothiazine tranquilizers and some antihistamines effective in motion sickness.

Over the last few years, I have been engaged in utilizing the narcotic antagonist naloxone (N-allylnoroxymorphone) in the treatment of itching, see U.S. Pat. No. 4,181,726 issued to me Jan. 1, 1980. Several of the patients I have treated for chronic itching had accompanying malignancies for which they were receiving systemic cancer chemotherapy. During each course of chemotherapy these patients would all experience extreme nausea and vomiting shortly after receiving intravenous chemotherapeutic agents.

Surprising, after I placed them on the naloxone for itching, they noted marked reduction in the nausea and vomiting associated with their chemotherapeutic treatment. Then I administered naloxone intravenously, subcutaneously, intramuscularly and orally to patients prior to receiving dicarbazine or adriamycin or methotrexate for treatment of malignant melanoma. The naloxone was given 10 minutes to 1 hour before intravenous dicarbazine, adriamycin or methotrexate was administered. Each patient had markedly reduced nausea and vomiting associated with the chemotherapy and two patients who had always become very nauseous and vomited many times before with dicarbazine had no nausea or vomiting after pretreatment with naloxone. Subsequently, I administered naloxone to several patients who had nausea and vomiting associated with a viral or bacterial gastroenteritis. The naloxone partially or completely relieved the nausea and vomiting of those patients.

Furthermore, I have found that naloxone administered intravenously, subcutaneously, or intramuscularly in total daily dosages of 0.4 to 20.0 mgs administered as a single dose or divided doses ranging from 0.4 mg. to 10 mg. 2–6 times daily, or oral administration of n-methyl cyclopropyl naloxone (naltrexone) administered in divided oral dosages of from 10 to 50 mg. up to 200 mg. daily, can prevent nausea or vomiting secondary to high dose oral antibiotic therapy or secondary to acute alcohol ingestion.

Naloxone is a narcotic antagonist which is not known to cause physical or psychological dependence and which exhibits essentially no pharmacological activity in non-addicts. Naloxone is normally given by injection to addicts to assist them in narcotic withdrawal and sometimes is administered to post operative patients for partial removal of narcotic depression following the use of narcotics during surgery. Surprisingly, it has been found that naloxone or a pharmaceutically acceptable salt thereof or a chemically similar narcotic antagonist such as the n-methyl cyclopropyl derivative are useful in the prophylaxis or treatment of nausea and/or emesis.

SUMMARY OF THE INVENTION

The present invention provides an improved method for prophylaxis or treatment of nausea and/or vomiting comprising administering a therapeutically effective amount of naloxone, n-methyl cyclopropyl naloxone, or a pharmaceutically acceptable salt thereof to a human patient in need of such treatment.

DETAILED DESCRIPTION OF PREFERRED EMBODIMENTS

Naloxone hydrochloride is commercially available from Endo Laboratories, Inc., a subsidiary of the DuPont Company, 1000 Stewart Avenue, Garden City, N.Y. 11530. The preparation of naloxone is described in U.S. Pat. No. 3,254,088.

In the practice of this invention, naloxone or a chemically similar narcotic antagonist is administered to patients either to prevent nausea and/or vomiting or to treat such symptoms. Naloxone is administered intraveneously, subcutaneously, and intramuscularly in total daily dosages of from 0.4 to 20.0 mgs. administered as a single dose or in divided doses ranging from 0.4 mg. to 10 mg. 2–6 times daily, and naloxone is administered orally in total daily dosages from 500 to 6,000 mgs. administered as a single dose or in divided doses ranging from 500 to 1000 mgs. 2–6 times daily for patients having cancer chemotherapy, for patients suffering from viral or bacterial gastroenteritis or from high dose oral antibiotic therapy or from alcohol ingestion. The n-methyl cyclopropyl derivative of naloxone (naltrexone) is administered in total daily dosages of from 10–200 mg. provided as a single oral dose or divided doses 2–6 times daily. The following examples further illustrate the invention.

EXAMPLE I 20 mg. of naloxone hydrochloride obtained from the Endo Pharmaceutical Company, was administered subcutaneously to a 49 year old white male suffering from malignant melanoma 10 minutes prior to the intravenous injection of dicarbazine. The patient noted only mild nausea over the two hours following dicarbazine therapy and had no episode of vomiting.

EXAMPLE II 15 mg. of naloxone hydrochloride obtained from the Endo Pharmaceutical Company, was administered subcutaneously to a 53 year old white female suffering from malignant melanoma 10 minutes prior to the intravenous injection of dicarbazine. The patient noted only mild nausea over the two hours following dicarbazine therapy and had no episode of vomiting.

EXAMPLE III 10 mg. of naloxone hydrochloride obtained from the Endo Pharmaceutical Company, was administered subcutaneously to a 53 year old white female suffering from malignant melanoma 10 minutes prior to the intravenous injection of dicarbazine. The patient noted only mild nausea over the two hours following dicarbazine therapy and had no episode of vomiting.

EXAMPLE IV 5 mg. of naloxone hydrochloride obtained from the Endo Pharmaceutical Company, was administered subcutaneously to a 53 year old white female suffering from malignant melanoma 10 minutes prior to the intravenous injection of dicarbazine. The patient noted only mild nausea over the two hours following dicarbazine therapy and had no episode of vomiting.

EXAMPLE V 2 mg. of naloxone hydrochloride obtained from the Endo Pharmaceutical Company, was administered intravenously to a 49 year old white male suffering from metastatic malignant melanoma 10 minutes prior to intravenous injection of dicarbazine. Unlike other times when he received dicarbazine the patient experienced no nausea and had no episode of emesis.

EXAMPLE VI 0.4 mg. naloxone hydrochloride obtained from the Endo Pharmaceutical Company, was administered intramuscularly to a 65 year old white male receiving systemic chlorambucil for disseminated mycosis fungoides. The patient's longstanding nausea associated with this chemotherapy was relieved.

EXAMPLE VII 1.2 mg. of naloxone hydrochloride obtained from the Endo Pharmaceutical Company, was administered subcutaneously to a 68 year old black male suffering from metastatic malignant melanoma 10 minutes prior to intravenous administration of dicarbazine. Unlike other times when he received dicarbazine the patient experienced no nausea and had no episode of emesis.

EXAMPLE VIII 2.4 mg. of naloxone hydrochloride obtained from the Endo Pharmaceutical Company, was administered subcutaneously in six divided doses of 0.04 mg. to a 36 year old white male suffering from metastatic malignant melanoma 10 minutes prior to the intravenous injection of dicarbazine and every 4 hours for 24 hours. The patient noted only mild nausea over the entire 24 hour period following dicarbazine therapy and had no episode of vomiting.

EXAMPLE IX 1000 mg. of naloxone hydrochloride obtained from the Endo Pharmaceutical Company, was administered every 6 hours orally to a 35 year old white female experiencing nausea and vomiting from a viral gastroenteritis. The unpleasant symptoms of nausea and vomiting were relieved within 30 minutes and the naloxone therapy provided complete relief from the vomiting and amelioration of the nausea for the two days of therapy.

EXAMPLE X 500 mg. of naloxone hydrochloride obtained from the Endo Pharmaceutical Company, was administered orally every 4 hours for one day to a 37 year old white male suffering from a viral gastroenteritis with nausea and vomiting. Within 30 minutes of administration vomiting ceased and the patient's nausea was markedly relieved. The relief was maintained over the entire day.

EXAMPLE XI 40 mg. of naltrexone obtained from the Endo Pharmaceutical Company, was administered orally to a 53 year old white female suffering from malignant melanoma 6 hours prior to the intravenous injection of dicarbazine. The patient noted no nausea during that day.

EXAMPLE XII 100 mg. of naltrexone obtained from the Endo Pharmaceutical Company, was administered orally to a 49 year old white male suffering from malignant melanoma, 4 hours prior to the intravenous injection of dicarbazine. The patient noted only mild nausea over the next 4 hours and had no episodes of vomiting.

EXAMPLE XIII 20 mg. of naltrexone obtained from the Endo Pharmaceutical Company, taken every 8 hours by a 36 year old male with severe acne vulgaris who had been unable to tolerate 2 gms. of erythromycin daily due to nausea and vomiting. The patient was able to tolerate such oral erythromycin dosages for the 4 days he was on nathrexone.

EXAMPLE XIV 40 mg. of naltrexone obtained from the Endo Pharmaceutical Company, was administered orally 30 minutes before 4 subjects drank 120 ml 95% ethanol. None of the subjects experienced nausea or vomiting.

EXAMPLE XV 3.2 mg. naloxone hydrochloride obtained from the Endo Pharmaceutical Company, was administered subcutaneously twice daily for 2 days to a 23 year old patient with conglobate acne. Following the first dose of naloxone, a single 1 gm dose of tetracycline hydrochloride was administered orally without producing any nausea or vomiting.

EXAMPLE XVI 5 mg. of naloxone hydrochloride obtained from the Endo Pharmaceutical Company was administered intravenously to a 28 year old oriental prior to the ingestion of 120 ml ethanol. No nausea and vomiting were observed. However, 1 day later when the same volume of ethanol was provided without prior naloxone treatment, the patient experienced severe nausea and vomiting.

What is claimed is:

1. A method for prophylaxis or treatment of emesis and nausea associated with viral or bacterial gastroenteritis or cancer chemotherapy or high dose oral antibiotics or acute alcohol ingestion in human patients in need of such prophylaxis or treatment comprising administering a therapeutically effective amount of naloxone or n-methyl cyclopropyl naloxone or their pharmaceutically acceptable salts to said patients.

2. The method of claim 1, comprising administering naloxone by a parenteral route of administration.

3. The method of claim 2, wherein the therapeutically effective amount is not less than 0.4 mg.

4. The method of claim 2, wherein the therapeutically effective amount is in the range of from about 0.4 mg. per day to about 20 mg. per day.

5. The method of claim 2, wherein the therapeutically effective amount is administered in divided doses of from one to about six times per day and each dose is in the range of from about 0.4 mg. to about 20 mg.

6. The method of claim 1, comprising administering naloxone or n-methyl cyclopropyl naloxone or their pharmaceutically acceptable salts by the oral route of administration.

7. The method of claim 6, wherein naloxone or n-methyl cyclopropyl naloxone or their pharmaceutically acceptable salts is administered to a patient in need of such treatment in divided doses.

8. The method of claim 7, wherein each dose of naloxone is in range of from about 10 mg. to about 1000 mg. and doses are administered from one time per day to about six times per day.

9. The method of claim 7, wherein the chemical derivative is n-methyl cyclopropyl naloxone and each dose of n-methyl cyclopropyl naloxone is in the range of from about 10 mg. to about 200 mg. daily and doses are administered from one time per day to about six times per day.

* * * * *